United States Patent [19]

Wolter et al.

[11] Patent Number: 5,233,006
[45] Date of Patent: Aug. 3, 1993

[54] POLYMERIZABLE SILICIC ACID HETEROPOLYCONDENSATES AND THEIR APPLICATION

[75] Inventors: Herbert Wolter, Gerchsheim; Klaus Rose, Kitzingen; Christian Egger, Höchberg, all of Fed. Rep. of Germany

[73] Assignee: Fraunhofer-Gesellschaft zur Forderung der Angewandten Forschung E.V., Munich, Fed. Rep. of Germany

[21] Appl. No.: 680,929

[22] Filed: Apr. 5, 1991

[30] Foreign Application Priority Data

Apr. 5, 1990 [DE] Fed. Rep. of Germany ....... 4011044

[51] Int. Cl.$^5$ ............................................... C08G 77/06
[52] U.S. Cl. .......................................... 528/32; 528/30; 528/26; 528/35; 528/33; 528/39; 528/34; 526/279
[58] Field of Search ................. 528/30, 26, 32, 35, 528/33, 39, 34; 526/279

[56] References Cited

U.S. PATENT DOCUMENTS

| | | | |
|---|---|---|---|
| 3,440,302 | 4/1969 | Speier et al. | 528/30 |
| 4,491,650 | 1/1985 | Rizk et al. | 525/102 |
| 4,625,007 | 11/1986 | Ellis et al. | 526/279 |
| 4,754,012 | 6/1988 | Yoldas et al. | 528/30 |
| 5,079,312 | 1/1992 | Isozaki et al. | 525/479 |

*Primary Examiner*—John C. Bleutge
*Assistant Examiner*—M. Glass
*Attorney, Agent, or Firm*—Oblon, Spivak, McClelland, Maier & Neustadt

[57] ABSTRACT

Polycondensates modified with unsaturated organic groups on the basis of hydrolytically condensable compounds of silicon and optionally other elements from the group B, Al, P, Sn, Pb, the transition metals, the lanthanides and the actinides, in which 5 to 100 mole %, based on the monomer compounds, of the fundamental hydrolytically condensable compounds are selected from silanes of the general formula (I):

$$\{X_aR_bSi(R'(A_c)_{(4-a-b)}\}_xB \qquad (I)$$

in which the groups and indices have the following meaning:

X: hydrogen, halogen, hydroxy, alkoxyl acyloxy, alkyl carbonyl, alkoxycarbonyl or $-NR''_2$;
R: alkyl, alkenyl, aryl, alkaryl, or aralkyl;
R': alkylene, arylene or alkylene arylene;
R'': hydrogen, alkyl or aryl;
A: O, S, PR'', POR'', NHC(O)O or NHC(O)NR'';
B: straight chain or branched organic group, which is derived from a compound B' with at least one C=C double bond (for c=1 and A=NHC(O)O or NHC(O)NR''), or at least two C=C double bonds, and 5 to 50 carbon atoms;
a: 1, 2 or 3;
b: 0, 1 or 2;
c: 0 or 1;
x: whole number, whose maximum value corresponds to the number of double bonds in the compound B' minus 1, or is equal to the number of double bonds in compound B', when c=1 and A stands for NHC(O)O or NHC(O)NR''.

21 Claims, No Drawings

POLYMERIZABLE SILICIC ACID HETEROPOLYCONDENSATES AND THEIR APPLICATION

BACKGROUND OF THE INVENTION

1. Field of the Invention

The present invention relates to silicic acid (hetero)-polycondensates and their application. In particular, the present invention relates to polycondensates modified with unsaturated organic groups based on hydrolytically condensable compounds of silicon and optionally other elements.

2. Discussion of the Background

A large number of silicic acid (hetero)polycondensates, which are modified with organic groups, and process for their preparation (e.g., starting from hydrolytically condensable organosilanes according to the sol-gel method) are already known (see, e.g., DE-A-38 35 968 and 40 11 045). Such condensates are used for various applications, e.g., as molding compounds, paints for coatings, etc. However, due to the manifold possible applications of this class of substances, there is a constant need to modify the already known condensates, on the one hand, to open up in this manner a new field of application and, on the other hand, to optimize even more their properties for specific purposes.

SUMMARY OF THE INVENTION

Accordingly, one object of the present invention is to provide a new class of silicic acid (hetero) polycondensates. In particular, these new condensates are to exhibit a plurality of possible variations, especially with respect to the nature of the modifying organic groups contained therein.

Another object of the present invention is to provide polycondensates modified with unsaturated organic groups on the basis of hydrolytically condensable compounds of silicon and optionally other elements from the group B, Al, P, Sn, Pb, the transition metals, the lanthanides and the actinides, in which 5 to 100 mole percent, based on the monomer compounds, of the fundamental hydrolytically condensable compounds are selected from silanes of the general formula (I):

$$\{X_aR_bSi(R'(A)_c)_{(4-a-b)}\}_xB \quad (I)$$

in which the groups and indices have the following meanings:

- X: hydrogen, halogen, hydroxy, alkoxyl, acyloxy, alkylcarbonyl, alkoxycarbonyl or $-NR''_2$;
- R: alkyl, alkenyl, aryl, alkaryl, or aralkyl;
- R': alkylene, arylene or alkylene-arylene;
- R'': hydrogen, alkyl or aryl;
- A: O, S, PR'', POR'', NHC(O)O or NHC(O)NR'';
- B: straight chain or branched organic group, which is derived from a compound B' with at least one C=C double bond, for c=1 and A=NHC(O)O or NHC(O)NR'', or at least two C=C double bonds, and 5 to 50 carbon atoms;
- a: 1, 2 or 3;
- b: 0, 1 or 2;
- c: 0 or 1;
- x: whole number, whose maximum value corresponds to the number of double bonds in compound B' minus 1, or is equal to the number of double bonds in compound B', when c=1 and A stands for NHC(O)O or NHC(O)NR''.

Another object of the present invention is a process to prepare the above polycondensates in which one or more hydrolytically condensable compounds of silicon and optionally other elements from the group B, Al, P, Sn, Pb, the transition metals, the lanthanides and the actinides, and/or precondensates derived from the aforementioned compounds are condensed hydrolytically, optionally in the presence of a catalyst and/or a solvent through the effect of water or moisture, where 5 to 100 mole percent, based on the monomer compounds, of the hydrolytically condensable monomers are selected from silanes of the above general formula (I).

Finally the object of this invention is also a process to prepare a coating paint or a molding compound (e.g., for injection molding) from the above polycondensates and the products obtained.

DETAILED DESCRIPTION OF THE PREFERRED EMBODIMENTS

The polycondensates of the invention are characterized especially by the fact that in the silanes on which they are based of the general formula (I), the distance between the silicon and the reactive double bond may be set in any arbitrary manner. These silanes (and thus also the polycondensates) may contain several reactive double bonds with the possibility of a three dimensional crosslinking and other functional groups, which allow a targeted adaptation of the polycondensates of the invention to the desired field of application. When the possible variations for the starting materials that differ from the silanes of the general formula (I) are taken into consideration, it becomes apparent that with the products of the invention a class of polycondensates is made available that can be adapted in a number of ways to specified fields of application and that can, therefore, be used in all areas in which silicic acid (hetero)polycondensates were already used before, yet also open up new possible applications, e.g., in the field of optics, electronics, medicine, etc.

The groups, specified in the above general formula (I) and in the other general formulas listed below, have in particular the following meanings. Alkyl groups are, e.g., straight chain, branched or cyclic groups having 1 to 20, preferably 1 to 10 carbon atoms and preferably lower alkyl groups having 1 to 6, preferably 1 to 4 carbons atoms. Specific examples are methyl, ethyl, n-propyl, isopropyl, n-butyl, sec-butyl, tert-butyl, isobutyl, n-pentyl, n-hexyl, cyclohexyl, 2-ethylhexyl, dodecyl and octadecyl.

The alkenyl groups are, e.g., straight chain, branched or cyclic groups having 2 to 20, preferably 2 to 10 carbon atoms and preferably lower alkenyl groups having 2 to 6 carbon atoms, like vinyl, allyl, and 2-butenyl.

Preferred aryl groups are phenyl, bisphenyl and naphthyl. The alkoxy, acyloxy, alkylamino, dialkylamino, alkylcarbonyl, alkoxycarbonyl, aralkyl, alkaryl, alkylene, arylene and alkylene arylene groups are derived preferably from the aforementioned alkyl and aryl groups. Specific examples are methoxy, ethoxy, n- and i-propoxy, n-, i-, sec- and tertbutoxy, monomethylamino, dimethylamino, diethylamino, N-ethylanilino, acetyloxy, propionyloxy, methylcarbonyl, ethylcarbonyl, methoxycarbonyl, ethoxycarbonyl, benzyl, 2-phenylethyl and tolyl.

The groups cited may optionally carry one or more substituents, e.g., halogen, alkyl, hydroxyalkyl, alkoxy, aryl, aryloxy, alkylcarbonyl, alkoxycarbonyl, furfuryl, tetrahydrofurfuryl, amino, monoalkylamino, dialkylamino, trialkylammonium, amido, hydroxy, formyl, carboxy, mercapto, cyano, nitro, epoxy, $SO_3H$ or $PO_4H_2$.

Among the halogens, fluorine, chlorine and bromine and in particular chlorine are preferred.

The following applies especially to the general formula (I): For $a \geq 2$ or $b=2$, the X and R groups can have the same or a different meaning.

In the preferred silanes of the general formula (I), X, R, R', A, a, b, c and x are defined as follows.

X: $(C_1-C_4)$-alkoxy, in particular methoxy and ethoxy; or halogen, in particular chlorine;
R: $(C_1-C_4)$-alkyl, in particular methyl and ethyl;
R': $(C_1-C_4)$-alkylene, in particular methylene and propylene;
A: O or S, in particular S;
a: 1, 2 or 3; $(4-a-b)$: 0 for $c=0$ and 1 for $c=1$;
c: 0 or 1, preferably 1;
x: 1 or 2.

It is especially preferred if the structural unit with the index x is selected from triethoxysilyl, methyl-diethomysilyl, methyl-dichlorosilyl, 3-methyl-dimethoxysilyl-propylthio, 3-trimethoxysilyl-propylthio, methyl-diethoxysilyl-methylthio and ethoxy-dimethylsilyl-methylthio.

The group B is derived from a substituted or unsubstituted compound B' with at least one or at least two C=C double bonds, e.g., vinyl, allyl, acrylic and/or methacrylic groups, and 5 to 50, preferably 6 to 30 carbon atoms. Preferably B is derived from a substituted or unsubstituted compound B' with two or more acrylate and/or methacrylate groups (such compounds are called (meth)acrylates in the following).

If the compound B' is substituted, the substituents can be selected among the aforementioned substituents.

To prepare the mono(meth)acryloxysilanes used according to the invention as the starting materials, compounds B' with two C=C double bonds are added; to prepare poly(meth)acryloxysilanes, those with at least three C=C double bonds are added. Specific examples of such compounds are the following (meth)acrylates:

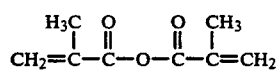

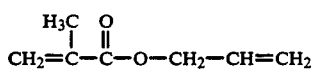

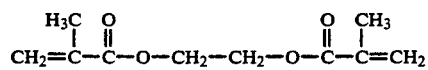

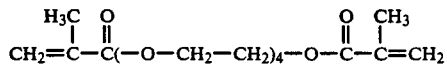

-continued

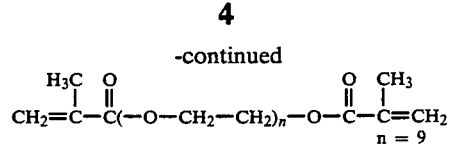
n = 9

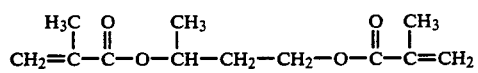

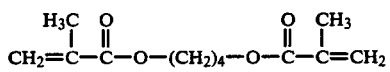

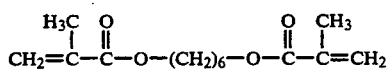

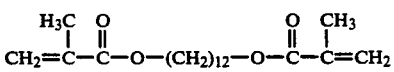

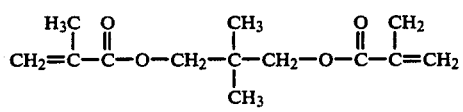

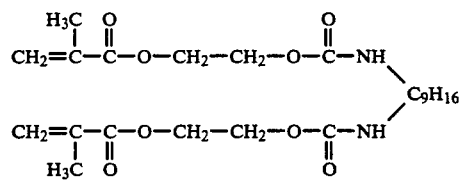

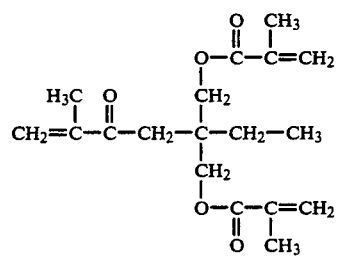

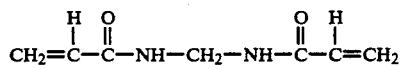

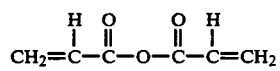

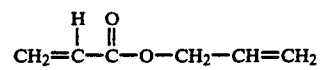

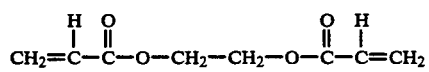

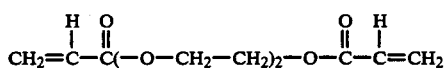

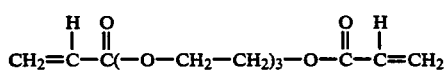

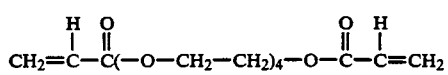

n = 9

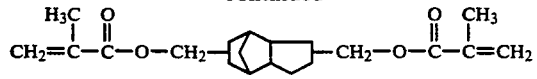

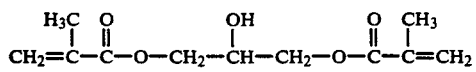

Preferred acrylates are, e.g., the acrylates Of trimethylol propane, pentaerythritol and dipentaerythritol. Examples include trimethylol propane triacrylate (TMPTA), pentaerythritol triacrylate (PETA), pentaerythritol tetracrylate and dipentaerythritol pentaacrylate.

Other examples for preferred (meth)acrylates are those of the formula

where E stands for H or $CH_3$ and D is an organic group, as contained, e.g., in the aforementioned specific compounds and/or in the compounds described in the following examples.

Thus, D can be derived, e.g., from $C_2$–$C_6$-alkanediols (e.g., ethyleneglycol, propyleneglycol, butyleneglycol, 1,6-hexanediol), polyethylene glycols or polypropylene glycols (e.g., those of formula HO—($CH_2$—$CHR'''$—O)$_n$H, where $R'''$ is H or $CH_3$ and $n=2$–$10$) or from optionally substituted and/or alkoxylated (e.g., ethoxylated and/or propoxylated) bisphenol A.

The silanes of the general formula (I) can be prepared, for example by a process where a) a silane of the general formula (II):

$$X_aR_bSiR'Y \qquad (II)$$

in which X, R, R', a and b have the aforementioned meanings, $(a+b)=3$ and Y denotes the group SH, PR''H or POR''H, is subjected to an addition reaction with a compound B' having at least two C=C double bonds; or b) a silane of the general formula (III):

$$X_aR_bSiR'NCO \qquad (III)$$

in which X, R, R', a and b have the aforementioned meanings and $(a+b)=3$, is subjected to a condensation reaction with a hydroxyl or amino-substituted compound B' having at least one C=C double bond; or c) a silane of the general formula (IV):

$$X_aR_bSiH \qquad (IV)$$

in which X, R, R', a and b have the aforementioned meanings and $(a+b)=3$, is subjected to a hydrosilylation reaction with a compound B' having at least two C=C double bonds.

The silanes of the general formulas (II) to (IV) are either commercially available or can be prepared according to known methods. W. Noll, "Chemie und Technologie der Silicone", Verlag Chemie GmbH, Weinheim/Bergstrasse (1968).

In process embodiment (a) the silanization takes place by means of one of the C=C double bonds of the compounds B', where, e.g., the mercapto group of a corresponding silane is added in a base catalyzed Michael reaction, forming a thioether unit. The phosphine is added in an analogous manner.

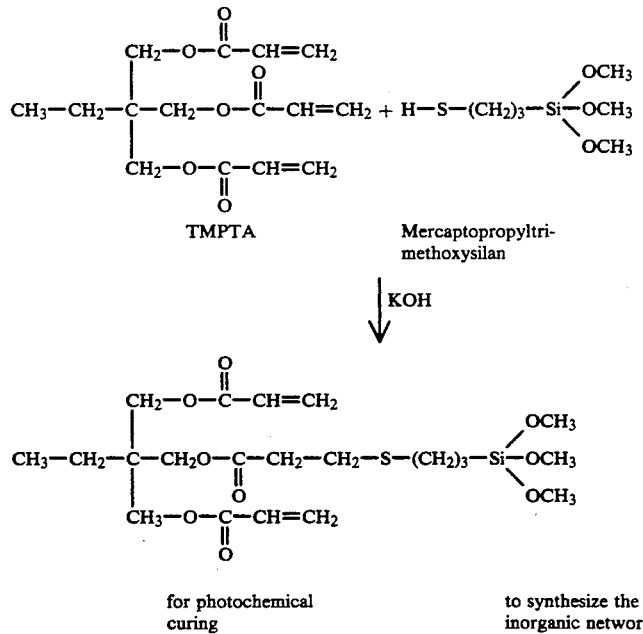

In process embodiment (b), a urethane (or urea) structure is produced through silanization of the hydroxyl or amino-substituted starting compound B' with an isocyanatosilane.

FIG. 2. Reaction involving formation of a urethane

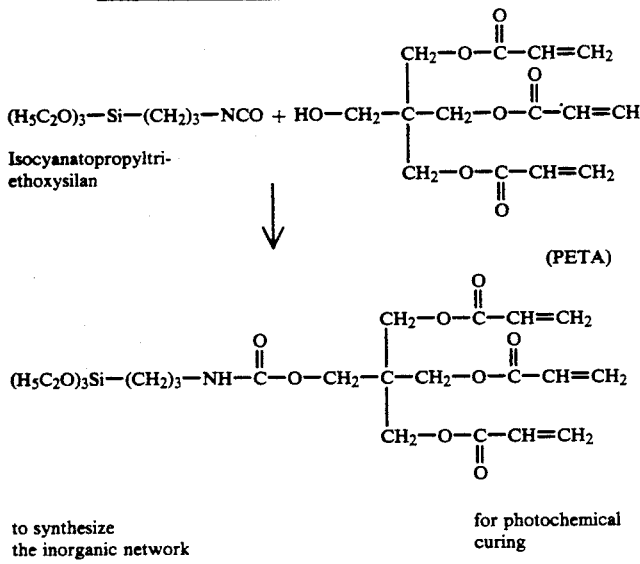

In process embodiment (c) the hydrosilylation takes place schematically according to the following reaction equation:

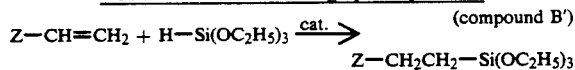

To prepare the polycondensates of the invention, the silanes of formula (I), prepared as above, do not have to be necessarily isolated. Rather it is even preferred to prepare these silanes first in a one-pot process and then to condense hydrolytically, optionally, following the addition of other hydrolyzable compounds.

In addition to the silanes of the general formula (I), still other hydrolytically condensable compounds of silicon and/or the aforementioned elements (preferably Al, Ti, Zr, V, B, Sn and/or Pb and especially preferred Al, Ti, Zr, and V) can be used either as such or already in precondensed form to prepare the polycondensates of the invention.

It is preferred that at least 50 mole percent, in particular at least 80 mole percent and specifically at least 90 mole percent, based on the monomer compounds, of the starting materials used to prepare the polycondensates of the invention are silicon compounds.

Similarly it is preferred that the polycondensates of the invention are based on at least 10 mole percent, e.g., 25 to 100 mole percent, in particular 50 to 100 mole percent and specifically 75 to 100 mole percent, based on the monomer compounds respectively, of one or more silanes of the general formula (I).

Among the hydrolytically condensable silicon compounds, which are different from the silanes of the general formula (I) and which can optionally be added, those of the general formula (V) are especially preferred:

in which X and R are defined as above, a' is a whole number from 1 to 4, in particular 2 to 4, and b' stands for 0, 1, 2 or 3, preferably 0, 1 or 2.

Especially preferred compounds of the general formula (V) are those in which the X group, which can be the same or different, are selected from halogen (F, Cl, Br and I, in particular Cl and Br), alkoxy (in particular $C_{1-4}$-alkoxy, such as methoxy, ethoxy, n-propoxy, i-propoxy and butoxy), aryloxy (in particular $C_{6-10}$-aryloxy, e.g., phenoxy), acyloxy (in particular $C_{1-4}$-acyloxy such as acetoxy and propionyloxy) and hydroxy, the R group, which can be the same or different, are selected from alkyl, (in particular $C_{1-4}$-alkyl such as methyl, ethyl, propyl and butyl), alkenyl (in particular $C_{2-4}$-alkenyl such as vinyl, 1-propenyl, 2-propenyl and butenyl), alkynyl (in particular $C_{2-4}$-alkynyl such as acetylenyl and propargyl) and aryl (in particular $C_{4-10}$-aryl, such as phenyl and naphthyl), where the aforementioned groups (with the exception of halogen and hydroxy) can exhibit, optionally, one or more inert substituents under the reaction conditions such as halogen and alkoxy. The above alkyl groups also include the corresponding cyclic and aryl-substituted groups such as cyclohexyl and benzyl, whereas the alkenyl and alkynyl groups can also be cyclic and the cited aryl groups are also to include alkaryl groups (like tolyl and xylyl).

In addition to the aforementioned especially preferred X groups, examples of other groups that are also suitable are hydrogen and alkoxy groups having 5 to 20, in particular 5 to 10 carbon atoms, and halogen and alkoxy-substituted alkoxy groups (such as B-methoxyethoxy). Other suitable R groups are straight chain, branched or cyclic alkyl, alkenyl and alkynyl groups having 5 to 20, in particular 5 to 10 carbon atoms such as n-pentyl, n-hexyl, dodecyl and octadecyl, and groups, which contain epoxy, mercapto or amino groups.

The following applies both to compounds of the general formula (I) and to those of the general formula (V).

Since the X groups are not present in the final product but rather are lost through hydrolysis, where as a rule the hydrolysis product must also be removed sooner or later in any suitable manner, X groups are especially preferred that carry no substituent and lead to hydrolysis products having a low molecular weight such as lower alcohols, like methanol, ethanol, propanol, n-, i-, sec- and tert-butanol.

The compounds of formulas (I) and (V) can be used totally or partially in the form of precondensates, i.e., compounds, which are produced through partial hydrolysis of the compounds of the formulas (I) and (V), either alone or in mixture with other hydrolyzable compounds, as described in detail below. Such oligomers that are preferably soluble in the reaction medium, can be straight chain or cyclic, low molecular weight partial condensates (polyorganosiloxanes) having a degree of condensation that ranges, e.g., from about 2 to 100 (e.g., 2 to 20, in particular about 6 to 10).

Examples of (largely commercial) compounds of the general formula (V), which are added preferably according to the invention, are the compounds of the following formula:

Si(OCH$_3$)$_4$, Si(OC$_2$H$_5$)$_4$, Si(O-n- oder i-C$_3$H$_7$)$_4$
Si(OC$_4$H$_9$)$_4$, SiCl$_4$, HSiCl$_3$, Si(OOCCH$_3$)$_4$
CH$_3$—SiCl$_3$, CH$_3$—Si(OC$_2$H$_5$)$_3$, C$_2$H$_5$—SiCl$_3$,
C$_2$H$_5$—Si(OC$_2$H$_5$)$_3$, C$_3$H$_7$—Si(OCH$_3$)$_3$, C$_6$H$_5$—Si(OCH$_3$)$_3$,
C$_6$H$_5$—Si(OC$_2$H$_5$)$_3$, (CH$_3$O)$_3$Si—C$_3$H$_6$—Cl,
(CH$_3$)$_2$SiCl$_2$, (CH$_3$)$_2$Si(OCH$_3$)$_2$, (CH$_3$)$_2$Si(OC$_2$H$_5$)$_2$,
(CH$_3$)$_2$Si(OH)$_2$, (C$_6$H$_5$)$_2$SiCl$_2$, (C$_6$H$_5$)$_2$Si(OCH$_3$)$_2$,
(C$_6$H$_5$)$_2$Si(OC$_2$H$_5$)$_2$, (i-C$_3$H$_7$)$_3$SiOH,
CH$_2$=CH—Si(OOCCH$_3$)$_3$, CH$_2$=CH—SiCl$_3$,
CH$_2$=CH—Si(OCH$_3$)$_3$, CH$_2$=CH—Si(OC$_2$H$_5$)$_3$,
CH$_2$=CH—Si(OC$_2$H$_4$OCH$_3$)$_3$,
CH$_2$=CH—CH$_2$—Si(OCH$_3$)$_3$,
CH$_2$=CH—CH$_2$—Si(OC$_2$H$_5$)$_3$,
CH$_2$=CH—CH$_2$—Si(OOCCH$_3$)$_3$,
CH$_2$=C(CH$_3$)—COO—C$_3$H$_7$—Si(OCH$_3$)$_3$,
CH$_2$=C(CH$_3$)—COO—C$_3$H$_7$—Si(OC$_2$H$_5$)$_3$,
(C$_2$H$_5$O)$_3$Si—C$_6$H$_4$—NH$_2$,
CH$_3$(C$_2$H$_5$O)$_2$Si—(CH$_2$)$_4$—NH$_2$,
(C$_2$H$_5$O)$_3$Si—C$_3$H$_6$—NH$_2$,
(CH$_3$)$_2$(C$_2$H$_5$O)Si—CH$_2$—NH$_2$,
(C$_2$H$_5$O)$_3$Si—C$_3$H$_6$—CN, (CH$_3$O)$_3$Si—C$_4$H$_8$—SH,
(CH$_3$O)$_3$Si—C$_6$H$_{12}$—SH, (CH$_3$O)$_3$Si—C$_3$H$_6$—SH,
(C$_2$H$_5$O)$_3$Si—C$_3$H$_6$—SH,
(CH$_3$O)$_3$Si—C$_3$H$_6$—NH—C$_2$H$_4$—NH$_2$,
(CH$_3$O)$_3$Si—C$_3$H$_6$—NH—C$_2$H$_4$—NH—C$_2$H$_4$—NH$_2$,

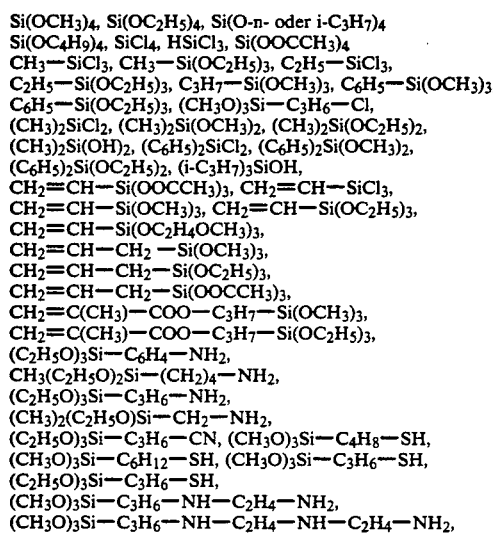

These silanes can be prepared according to known methods. See W. Noll, loc. cit.

The ratio of silicon compounds with four, three, two or one hydrolyzable X group (or also hydrolyzable compounds that are different from the silicon compounds) to one another is based primarily on the desired properties of the resulting polycondensates or the final products prepared from them.

Especially preferred among the hydrolyzable aluminum compounds used optionally to prepare the polycondensates are those that exhibit the general formula (VI):

AlX'$_3$ (VI)

in which the X' groups, which can be the same or different, are selected from halogen, alkoxy, alkoxycarbonyl and hydroxy. With respect to the more detailed (preferred) definition of these groups, reference can be made to the statements relating to the suitable hydrolyzable silicon compounds of the invention. The groups just cited can also be replaced totally or partially with chelate ligands (e.g., acetylacetone or acetoacetic ester, acetic acid).

Especially preferred aluminum compounds are the aluminum alkoxides and halides. Examples thereof are Al(OCH$_3$)$_3$, Al(OC$_2$H$_5$)$_3$, Al(O-n-C$_3$H$_7$)$_3$, Al(O-i-C$_3$H$_7$)$_3$, Al(OC$_4$H$_9$)$_3$, Al(O-i-C$_4$H$_9$)$_3$, Al(O-sec-C$_4$H$_9$)$_3$, AlCl$_3$, AlCl(OH)$_2$.

At room temperature liquid compounds, such as aluminum-sec-butylate and aluminum-isopropylate, are especially preferred.

Suitable hydrolyzable titanium and zirconium compounds, which can be added according to the invention, are those of the general formula (VII):

MX$_a$R$_b'$ (VII)

in which M denotes Ti or Zr and X, R, a' and b' are defined as in the case of the general formula (V). This also applies to the preferred meanings of X and R. Especially preferred are compounds of the formula (VII) in which a' is 4.

As in the case of the above Al compounds, complex Ti and Zr compounds can also be used. Here acrylic acid and methacrylic acid are additional preferred complexing agents.

Examples of the zirconium and titanium compounds that can be added according to the invention are the following:

TiCl$_4$, Ti(OC$_2$H$_5$)$_4$, Ti(OC$_3$H$_7$)$_4$, Ti(O-i-C$_3$H$_7$)$_4$,

Ti(OC$_4$H$_9$)$_4$, Ti(2-ethylhexoxy)$_4$; ZrCl$_4$, Zr(OC$_2$H$_5$)$_4$,

Zr(OC$_3$H$_7$)$_4$, Zn(O-i-C$_3$H$_7$)$_4$, Zr(OC$_4$H$_9$)$_4$, ZrOCl$_2$, and Zr(2-ethylhexoxy)$_4$.

Other hydrolyzable compounds, which can be added to prepare the polycondensates of the invention, are, e.g., boron trihalides and boric-acid esters (such as BCl$_3$, B(OCH$_3$)$_3$ and B(OC$_2$H$_5$)$_3$), tin tetrahalides and tin tetralkoxides (such as SnCl$_4$ and Sn(OCH$_3$)$_4$) and vanadyl compounds such as VOCl$_3$ and VO(OCH$_3$)$_3$.

To synthesize the polycondensates of the invention, the silanes of the general formula (I) are hydrolyzed and polycondensed with or without the addition of other cocondensable components. Polycondensation is conducted preferably according to the sol-gel process, as described in the DE-A-27 58 414, 27 58 415, 30 11 761, 38 26 715 and 38 35 968 and is explained in more detail below.

To synthesize an organic network, the polycondensates of the invention can be polymerized with or without the addition of other copolymerizable components (see below). Polymerization can take place, e.g., thermally or photochemically using methods that are described in the DE-A 31 43 820, 38 26 715 and 38 35 968 and are also explained in more detail below.

The course of polycondensation can be examined, e.g., by means of Karl-Fischer titration (determination of water consumption during hydrolysis); the course of the curing (e.g., photochemical) can be examined by means of IR spectroscopy (intensity and relation of the C=C and C=O bands).

As already stated, the polycondensates of the invention can be prepared by a method that is conventional in this field. If silicon compounds are used almost exclusively, the hydrolytic condensation can occur in most cases by adding (preferably while stirring and in the presence of a hydrolysis or condensation catalyst) the stoichiometrically required quantity of water or optionally excess water, at room temperature or under slight cooling, directly to the silicon compounds that are to be hydrolyzed and that are present either as such or dissolved in a suitable solvent; and the resulting mixture is then stirred for a period of time (one or more hours). In the presence of reactive compounds of Al, Ti and Zr it is generally recommended that the water be added in stages. Regardless of the reactivity of the compounds present, hydrolysis generally takes place at temperatures ranging from $-20°$ to $130°$ C., preferably from $0°$ C. to $30°$ C. or at the boiling point of the solvent that can be added as an option. As already stated, the best method of adding water depends primarily on the reactivity of the added starting compounds. Thus, the dissolved starting compounds can be added slowly drop-by-drop to an excess of water or water is added in a portion or in proportions to the starting compounds that are or are not dissolved. It may also be useful to add the water not as such, but rather to introduce it into the reaction system with the aid of water-containing organic or inorganic systems. In many cases it has proven to be especially suitable to introduce the quantities of water into the reaction mixture with the aid of moisture-laden adsorbents, e.g., molecular sieves, and water-containing organic solvents, e.g., 80% ethanol. Water can also be added by means of a reaction in which water is formed, e.g., during the formation of ester from acid and alcohol.

If a solvent is used, in addition to lower aliphatic alcohols (e.g., ethanol and isopropanol), ketones, preferably lower dialkyl ketones, like acetone and methyl isobutyl ketone, ethers, preferably lower dialky ethers, like diethyl ether and dibutyl ether, THF, amides, esters, in particular ethyl acetate, methyl formamide, and their mixtures are also suitable.

Hydrolysis and condensation catalysts added, according to the invention, not necessarily but still preferably, are compounds that split off protons. Examples thereof are organic and inorganic acids, like hydrochloric acid, formic acid and acetic acid, where hydrochloric acid is especially preferred as the catalyst. In the case of a basic catalyst, suitable catalysts are, e.g., $NH_3$, NaOH or KOH. Even catalysis with fluoride ions is possible, e.g., adding HF, KF or $NH_4F$.

The starting compounds do not all have to be necessarily already present at the start of the hydrolysis (polycondensation), but rather in specific cases it can even prove to be advantageous if only a part of these compounds is brought into contact first with water and later the remaining compounds are added.

In order to avoid as far as possible precipitations during hydrolysis and polycondensation especially when using hydrolyzable compounds that are different from the silicon compounds, in this case it is preferred to conduct the addition of water in several steps, e.g., in three steps. In so doing, one-tenth to one-twentieth of the quantity of water required stoichiometrically for hydrolysis is added in the first step. After stirring for a short period of time, one-fifth to one-tenth of the stoichiometric quantity of water is added; and after another short period of stirring, a stoichiometric quantity of water is finally added so that at the end there is a slight excess of water.

The condensation period depends on the respective starting components and their proportions, the optionally used catalyst, the reaction temperature, etc. In general polycondensation occurs at normal pressure; it can, however, also be conducted at raised or reduced pressure.

The polycondensate obtained thus, can be further processed either as such or after partial or almost total removal of the solvent used or of the solvent formed during the reaction. In some cases it can prove to be advantageous to replace, in the product obtained following polycondensation, the excess water and the solvent, which is formed and also optionally added, with another solvent, in order to stabilize the polycondensate. To this end, the reaction mixture can be thickened, e.g., in a vacuum at slightly raised temperature (up to a maximum of $80°$ C.) until it can still be absorbed without any problems with another solvent.

If the polycondensates of the invention are to be used as paints to coat, e.g., plastics such as PVC, polycarbonate, polymethylmethacrylate, polyethylene, polystyrene, etc., glass, paper, wood, ceramic, metal, etc., conventional paint additives such as coloring agents (pigments and dyes), fillers, oxidation inhibitors, flow control agents, ultraviolet absorbers, stabilizers and the like can also be added optionally to said polycondensates at the latest prior to application. Also, additives to increase the conductivity (e.g., graphite powder, silver powder, etc.) deserve to be mentioned in this respect. If used as a molding compound, the addition of inorganic and/or organic fillers such as (glass) fibers, minerals, etc., is especially suitable.

If curing with irradiation (UV or IR radiation) and/or thermal energy is intended, a suitable initiator can be added.

As photoinitiators, commercially available initiators can be added, for example. Examples thereof are IRGACURE 184 (1-hydroxycyclohexyl-phenyl-ketone), IRGACURE 500 (1-hydroxycyclohexyl-phenyl-ketone, benzophenone) and other photoinitiators of the IRGACURE type that can be obtained from Ciba-Geigy: DAROCUR 1173, 1116, 1398, 1174 and 1020 (obtainable from Merck), benzophenone, 2-chlorothioxanthone, 2-methylthioxanthone, 2-isopropylthioxanthone, benzoin, b 4,4'-dimethoxy benzoin, benzoin ethyl ether, benzoin isopropyl ether, benzyl dimethyl ketal, 1,1,1-trichloroacetophenone, diethoxyacetophenone, dibenzosuberone and camphorquinone. The latter initiator is especially suitable for irradiation with light in the visible range.

Suitable thermal initiators are especially organic peroxides in the form of diacyl peroxides, peroxydicarbonates, alkyl peresters, dialkyl peroxides, perketals, ketone peroxides and alkyl hydroperoxides. Preferred examples of thermal initiators are dibenzoyl peroxide, tert-butyl perbenzoate and azobisisobutyronitrile.

The initiator can be added in the usual quantities. Thus, an initiator in a quantity of, e.g., 0.5 to 5 percent by weight, in particular 1 to 3 percent by weight, based on the mixture, can be added to a mixture, which contains 30 to 5 percent by weight of a solid (polycondensate).

A paint, provided optionally with a photoinitiator and based on the polycondensates of the invention, can then be applied to a suitable substrate. For this coating process the usual coating methods can be used, e.g., dipping, flow coating, pouring, centrifuging, rolling, spraying, spreading, electrostatic spraying and electronic dipping. It should also be mentioned here that the paint does not necessarily have to contain solvents. Especially when using starting substances (silanes) with two alkoxy groups on the Si atom, the process can be conducted also without the addition of solvents.

Prior to curing, the applied paint is preferably left to dry. Thereafter, depending on the kind or presence of an initiator, it can be cured by a known method thermally or by irradiation (e.g., with a UV lamp, a laser, an electron beam source, a light source, which emits radiation in the visible range, etc.). Of course, combinations of these curing methods are also possible, e.g., UV/IR or UV/thermally.

Especially preferred is the curing of applied paint through irradiation in the presence of a photoinitiator. In this case it can prove to be advantageous to conduct a thermal curing following the radiation cure, especially in order to remove solvent that is still present or to include in the curing still other reactive groups. In particular epoxy groups respond in this respect to a thermal treatment better than to an irradiation treatment.

Even though there are already unsaturated groups (at least those that are derived from the B group) in the polycondensates of the invention, it can prove to be advantageous in specific cases to add still other compounds (preferably of a purely organic nature) with unsaturated groups to the products of the invention before or during their further processing (curing). Preferred examples of such compounds are compounds B', (meth)acrylic acid and compounds derived thereof, in particular (meth)acrylates of (preferably monovalent) alcohols (e.g., $C_{1-4}$-alkanols), methacrylonitrile, styrene and mixtures thereof. If the polycondensates of the invention are used for the preparation of a coating paint, such compounds can act simultaneously as solutions or diluents.

Molded parts on the basis of the polycondensates of the invention or molding compounds can be prepared with any of the usable methods in this field, e.g., injection molding, mold pouring, extrusion, etc. The products of the invention are also suitable to manufacture composite materials (e.g., with glass fiber reinforcement).

The polycondensates of the invention represent highly reactive systems, which cure into mechanically stable coatings, e.g., with ultraviolet irradiation within fractions of a second. Even the cure into molded parts can take place in the range of a few seconds to minutes.

They can be prepared by means of simple condensation reactions, and by suitably selecting the starting compounds (especially those of the general formula (I)) they can exhibit a variable number of reactive groups with the most variable functionality.

The mechanical (e.g., flexibility, scratch and abrasion resistance) and physical-chemical properties (adsorption, color, absorption characteristics, refractive index, adhesion, wetting characteristics etc.) of the products can be affected by means of the number of hydrolyzable groups in the starting silanes, the distance between the silicon atom and the functional organic groups, i.e., by means of the chain length, and by means of the presence of other functional groups in this chain.

Depending on the type and number of the hydrolyzable groups (e.g., alkoxy groups), silicone or glass-like properties can be obtained in the polycondensates of the invention and the final products manufactured thereof.

The polycondensates of the invention are suitable, e.g., for use as or in coating, filler or bulk materials, adhesive(s), coupling agent(s), sealants, and injection molding compounds. Coatings and molded parts made of the polycondensates of the invention have the advantage that they can be photochemically structured (see, e.g., DE-A-38 35 968). Specific fields of application are, e.g., the coating of substrates made of metal, plastic, paper, ceramic, wood, glass, textiles etc., by dipping, pouring, spreading, spraying, electrostatic spraying, electronic dipping, etc., and uses for optical, optoelectric or electronic components. Even the possible use to prepare scratch-resistant, abrasion-resistant and/or corrosion protective coatings deserves mention in this respect.

Other features of the invention will become apparent in the course of the following descriptions of exemplary embodiments which are given for illustration of the invention and are not intended to be limiting thereof.

EXAMPLES

The following starting materials are used in these preparation examples;

silane I: $HS-(CH_2)_3-SiCH_3(OCH_3)_2$
silane II: $HS-CH_2-SiCH_3(OC_2H_5)_2$
silane III: $HS-(CH_2)_3-Si(OCH_3)_3$
silane IV: $HSiCH_3(OC_2H_5)_2$
silane V: $HSi(OC_2H_5)_3$
silane VI: $HSiCH_3Cl_2$
silane VII: $HS-CH_2-Si(CH_3)_2OC_2H_5$
silane VIII: $OCN-(CH_2)_3-Si(OC_2H_5)_3$
acrylate A: 1,6-hexanediol diacrylate
acrylate B: tripropylene glycol diacrylate
acrylate C: 2,2-di[4-(2-hydroxyethoxy)phenyl]-propanediacrylate
acrylate D: di(trimethylolpropane)tetraacrylate
acrylate E: 1,2,3-tri(3-hydroxypropoxy)propane triacrylate
acrylate F: tris(2-hydroxyethyl)isocyanurate triacrylate
acrylate G: 2,2-di[4-(2-hydroxyethoxy)phenyl]propane dimethacrylate
acrylate H: 2,2-di[3,5-dibromo-4-(2-hydroxyethoxy)-phenyl]propane dimethacrylate
acrylate I: pentaerythritol tetraacrylate
acrylate J: trimethylol propane triacrylate
acrylate K: pentaerythritol triacrylate
acrylate L: dipentaerythritol pentaacrylate
acrylate M: bisphenol-A-dimethacrylate
acrylate N: trimethylol propane trimethacrylate
acrylate O: glycerol-1,3-dimethacrylate

EXAMPLE 1

Preparation of the Compound of the Formula $$CH_2=CH-\underset{\underset{O}{\|}}{C}-O-CH_2$$
$$H_5C_2-\underset{|}{\overset{|}{C}}-CH_2-O-\underset{\underset{}{\|}}{\overset{O}{C}}-CH_2-CH_2-Si(OC_2H_5)_3$$
$$CH_2=CH-\underset{\underset{O}{\|}}{C}-O-CH_2$$

Compound (1)

0.1 mole (29.5 g, 26.6 ml) acrylate J were reacted with 0.1 mole (16.5 g, 18.8 ml) silane V in 100 ml of solvent (e.g., ethanol, benzene, cyclohexane, diethyl ether or methyltert.-butyl ether). To this solution were added 0.3 mmol (930 mg) of the catalyst ([Rh(CO)Cl(PPh$_2$CH$_2$CH$_2$SiO$_{1.5}$]40 SiO$_2$ (BET surface urea=723.5 m$^2$, average pore radius 1.94 nm, average pore volume 0.70 cm$^3$/g) and stirred in the dark at 40°±3° C. until in the IR spectrum no more Si-H vibrations could be detected (48 to 72 hours). Following completion of the reaction, the catalyst was filtered off and the solvent was removed in vacuum.

Yield 43.5 g (94%) of the yellowish, light-sensitive oil, boiling point 202° C. (decomposition).

| C$_{21}$H$_{36}$O$_9$Si | molecular weight: 460.60 |
|---|---|

| calculated: | C 54.76% | H 7.88% |
|---|---|---|
| found: | C 56.02% | H 7.69% |

$^1$H-NMR (CDCl$_3$): δ=5.6–7.1 (m;—CH═CH$_2$;6H)
3.2–4.2 (m;—OCH$_2$—;12H)
2.0–2.5 (t;—CH$_2$COO—;2H)
0.3–1.8 (m;—CH$_3$,—CH$_2$—;16H)
$^{29}$Si-NMR (CDCl$_3$): δ=−24.1 (s)

EXAMPLE 2

Preparation of the Compound of the Formula

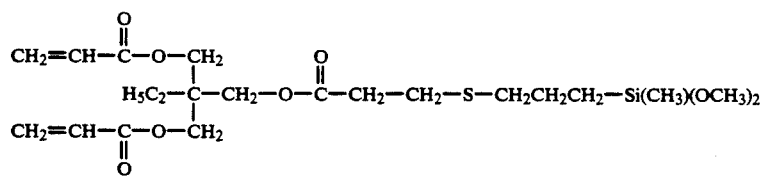

Compound (2)

0.15 mole (44.45 g) acrylate J were introduced under nitrogen protection while cooling in a water bath to 20° C. and quickly reacted with 0.15 mole (27.05 g) silane I and 0.0015 mole (0.0842 g) KOH in 6 g of ethanol. The reaction mixture was stirred for 5 minutes (iodine-mercaptan test), then taken up in 200 ml of diethyl ether, shaken, and washed repeatedly with 20 ml of H$_2$O until the wash water reacted neutrally. The ether phase was dried, e.g., over Na$_2$SO$_4$ or with a hydrophobic filter and concentrated by evaporation at 35°–40° C. under separator vacuum. Finally the residue was dried for about 1 hour in a high vacuum at 35°–40° C.

EXAMPLE 3

Preparation of the Compound of the Formula

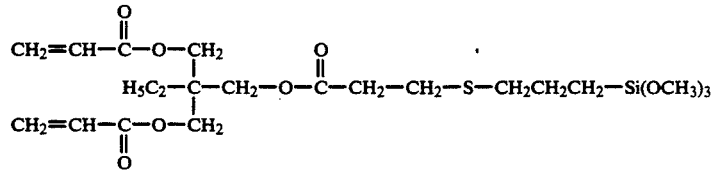

Compound 3

The preparation was conducted as in preparation Example 2 using an equimolar quantity of silane III instead of silane I.

EXAMPLE 4

Preparation of the Compound of the Formula

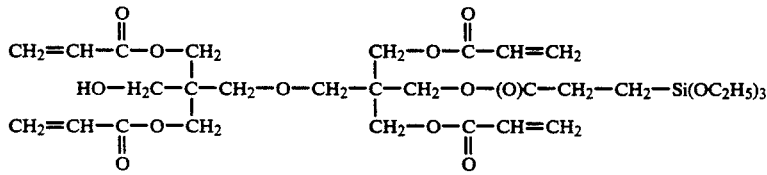

Compound 4

The preparation was conducted as in preparation Example 1 using an equimolar quantity of acrylate L instead of acrylate J. A yellowish, light sensitive oil was obtained.

| C$_{31}$H$_{47}$O$_{15}$Si | molecular weight: 687.80 | |
|---|---|---|
| calculated: | C 54.14% | H 6.89% |
| found: | C 54.47% | H 7.11% |

$^1$H-NMR (CDCl$_3$): δ=5.8–6.9 (m;—CH═CH$_2$;12H)
3.3–4.7 (m;—OCH$_2$—;22H)
2.2–2.8 (m;—CH$_2$COO,—OH;3H)
1.2 (t;—OCH$_2$CH$_3$;9H)
1.0 (t;—SiCH$_2$, 2H)
$^{29}$Si-NMR (CDCl$_3$): δ=−26.3 (s)

EXAMPLE 5

Preparation of the Compound of the Formula

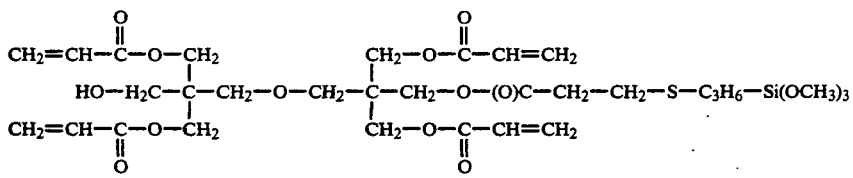

Compound (5)

The preparation was conducted as in preparation Example 3 using an equimolar quantity of acrylate L instead of acrylate J.

EXAMPLE 6

Alternative Preparation of the Compound 2 of Preparation Example 2

18 g (0.1 mole) silane I were added to 29.6 g (0.1 mole) acrylate J, dissolved in 50 ml of ethyl acetate, at 5° C. (ice cooling) under a nitrogen atmosphere. Again at 5° C. and under nitrogen atmosphere the resulting mixture was slowly reacted (drop-by-drop) with 0.0561 g (0.001 mole) KOH, dissolved in 5 g of ethanol. In so doing, the feed velocity was set in such a manner that the temperature of the reaction mixture remained clearly under 40° C. After a few minutes of stirring at 5° C., the reaction was checked (with the absence of free mercaptosilane; the iodine-mercaptan test is negative). Following completion of the reaction, the reaction mixture was reacted with 50 ml of ethyl acetate and washed with 30 ml portions of water until the eluate reacted neutrally. The organic phase was then dried over $Na_2SO_4$ or filtered over a hydrophobic filter, subsequently concentrated by evaporation at 30° C. by rotary evaporator and subsequently dried at 20°-30° in the high vacuum. Yield 44 g=93% (solid content 99%).

According to the process described in the above examples, the following silanes of the invention of the general formula (I) (1:1 adducts) were obtained. The silanes are characterized by a Roman numeral (starting silane) and a letter (starting acrylate).

| | |
|---|---|
| II-A | (compound 6) |
| I-A | (compound 7) |
| II-B | (compound 8) |
| I-B | (compound 9) |
| II-C | (compound 10) |
| I-C | (compound 11) |
| II-J | (compound 12) |
| I-E | (compound 13) |
| II-E | (compound 14) |
| I-F | (compound 15) |
| II-F | (compound 16) |
| IV-A | (compound 17) |
| V-A | (compound 18) |
| VI-J | (compound 19) |
| IV-J | (compound 20) |
| V-L | (2:1 adduct) (compound 21) |
| VII-J | (compound 22) |
| I-M | (compound 23) |
| I-H | (compound 24) |
| I-D | (compound 25) |
| III-K | (compound 26) |
| I-I | (compound 27) |
| I-L | (compound 28) |
| I-G | (compound 29) |
| I-N | (compound 30) |

Typical IR vibration bands of some of the above compounds are compiled in the following tables (absorbed as film between KBr sheets).

EXAMPLE 7

Preparation of the Compound of the Formula

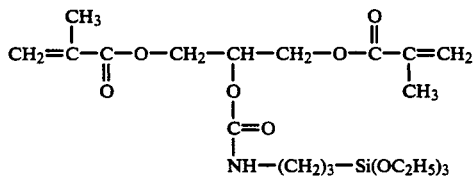

Compound (31)

Under a moisture-free atmosphere 12.4 g (0.05 mole) silane VIII were slowly added drop-by-drop to 11.4 g (0.05 mole) acrylate O and 1.6 g (0.0025 mole) dibutyl tin didodecanoate (or a equivalent quantity of 1,4-diazabicyclo[2.2.2]octane). In so doing, a heating of the reaction mixture was observed. The reaction ended after about 1 hour (IR check, absence of free NCO groups). The desired compound was isolated in known manner. IR (film): 3,380 (broad $v_{N-H}$), 1,725 ($v_{C=O}$) and 1,640 ($v_{C=C}$)cm$^{-1}$.

EXAMPLE 8

While cooling to 5° C. (ice bath) and under a nitrogen atmosphere, 0.1 mole (18 g) of silane I were added to a solution of 0.1 mole (29.6 g) of acrylate L in 50 ml ethyl acetate, whereupon the mixture was reacted so slowly (dropwise) with 0.001 mole (0.056) KOH, dissolved in 5 g of ethanol that the temperature of the reaction mixture remained clearly under 40° C. After completion of the addition, the mixture was stirred for a few minutes more at 5° C. until the iodine-mercaptan test indicated the absence of free silane I. Then with ice cooling 0.1 mole (1.8 g) of water were added in the form of a 1 N HCl solution and subsequently the mixture was stirred for another 2 hours at 25° C. Subsequently the reaction mixture was diluted with ethyl acetate (50 ml) and washed with 30 ml portions of $H_2O$ until the wash water reacted neutrally. The washed organic phase was then dried over $Na_2SO_4$ or with the aid of a hydrophobic filter, whereupon the preparation was worked up according to different variants.

(a) An almost solvent-free polycondensate was obtained by evaporating the solution on a rotary evaporator at approximately 30° C. and subsequent treatment in a high vacuum at approximately 20° to 30° C. (approximately 1 hour). Solid content 95%; viscosity 17,200 mpa.s (25° C., rotational viscometer).

(b) Any arbitrary solid in the range of 30 to 80% and any arbitrary viscosity of the polycondensate solution, depending on the intended purpose, was set by evaporating the ethyl acetate solution on the rotary evaporator at approximately 30° C.

(c) The ethyl acetate solvent was replaced with another solvent by removing as far as possible the ethyl acetate on the rotary evaporator at approximately 30° C. and thereupon adding another solvent (e.g., ethanol, acetone, toluene, diethyl ether, THF, etc.) in such quantities that the desired solid content or the desired viscosity of the solution was reached.

EXAMPLE 9

The procedure was the same as in Example 8, but acrylate J was replaced with an equivalent quantity (42.4 g) of acrylate C. During preparation according to variant (a), a polycondensate with a solid content of 95% and a viscosity of 115,000 mpa.s (25° C., rotational viscometer) was obtained.

EXAMPLE 10

Under a nitrogen atmosphere 100 mmol (16.4 g) of silane V and 0.15 mmol (0.59 g) of catalyst of the formula $(Rh(CO)ClP(C_6H_5)_2CH_2CH_2CH_2SiO_{3/2} \cdot SiO_2)$ were added to a solution of 50 mmol (26.5 g) of acrylate L in 100 ml of ethanol. The reaction mixture was stirred at 30° C. for 7 hours, whereupon the band in the IR spectrum had disappeared at 2,240 cm$^{-1}$ (Si—H). Subsequently the catalyst was filtered off and the filtrate was slowly reacted (dropwise) with 150 mmol (2.7 g) H$_2$O in the form of a 1 N HCl solution. The reaction mixture was stirred at approximately 25° C. for 3 hours, then filtered and evaporated on a rotary evaporator at approximately 30° C. until a solid content of 43% was obtained.

EXAMPLE 11

Under a nitrogen atmosphere 0.1 mole (18.03 g) of silane I were added dropwise to 0.1 mole (33.9 g) of acrylate N, dissolved in 100 ml of ethyl acetate, followed by the slow addition (dropwise) of a solution of 0.01 mole (0.56 g) KOH in ethanol while cooling (ice bath). After about 5 minutes the reaction (thiol addition) was terminated. For the purpose of hydrolysis and condensation, 1.8 g of 5.7 N HCl were subsequently added drop-by-drop, whereupon the mixture was stirred at room temperature for 20 hours. Then the reaction mixture was washed first with diluted aqueous NaOH and then with distilled H$_2$O. Following filtration, the mixture was evaporated at approximately 30° C. on the rotary evaporator and the remaining volatile components were removed under oil pump vacuum at room temperature. A colorless, transparent product having a viscosity of 1,760 mpa.s (25° C., rotational Viscometer) remained.

EXAMPLE 12

The procedure was the same as in Example 11, but using 0.4 mole (118.5 g) of acrylate J in 400 mol of ethyl acetate, 0.4 mole (72.14 g) of silane I, 0.004 mole (0.224 g) KOH in ethanol and 7.2 g of 0.7 N HCl. A light-yellowish, transparent resin having a viscosity of 9,500 to 13,000 mpa.s at 25° C. (depending on the precise synthesis conditions) remained.

EXAMPLE 13

Other polycondensates were prepared analogously to Example 11 and the viscosities of the resins obtained were measured. They are compiled in the following tables.

| Polycondensate from Compound no. (See Preparation Examples) | Viscosity at 25° C., Rotational Viscometer (Mpa.s) |
| --- | --- |
| 12 | 12,300 |
| 22 | 7,200 |
| 13 | 4,700–6,600 (depending on the precise synthesis conditions) |
| 29 | 3,200 |

EXAMPLE 14

The polycondensate solution obtained in Example 10 was reacted with 3 percent by weight, based on the polycondensate, of a UV initiator (IRGACURE ® 907) and then applied with a film draw carriage on a sheet made of polymethyl methacrylate. Thereupon curing of the resulting coating was accomplished by UV irradiation (lamp output 2,000 W). The curing periods, the layer thicknesses of the cured coatings and the abrasion after cycles with the Taber abraser are shown in the following Table 1.

TABLE 1

| Irradiation Period (s) | Layer Thickness (μm) | Abrasion After 100 Cycles (%) |
| --- | --- | --- |
| 0.1 | 13 | 6.7 |
| 0.5 | 17 | 4.5 |
| 5 | 18 | 3.0 |

As apparent from the results, the polycondensates of the invention can be cured into protective coatings with significant abrasion resistance by irradiation in fractions of a second. Of course, even better coatings can be obtained by longer irradiation periods and/or other suitable measures (increase in the quantity of initiator or the radiator output).

EXAMPLE 15

The almost solvent-free polycondensate of Example 9 was applied with a split knife on a glass plate after the addition of a UV initiator and cured with UV irradiation (radiator output 2,000 W). In the following Table 2, the kind and quantity of the UV initiator, the irradiation periods, the resulting layer thicknesses and the abrasion values after 100 cycles (Taber abraser) are compiled.

TABLE 2

| UV Initiator | Quantity of Initiator (wt. %) | Irradiation Period (s) | Layer Thickness (μM) | Abrasion After 100 cycles (%) |
| --- | --- | --- | --- | --- |
| IRGACURE ® 907 | 5 | 0.5 | 20 | 5 |
| IRGACURE ® 369 | 3 | 0.5 | 30 | 7 |
| IRGACURE ® 369 | 3 | 0.1 | 30 | 10 | modulus of elasticity of the coatings: approximately 70 Mpa

In addition to the aforementioned satisfactory abrasion values at extremely short periods of irradiation, the added polycondensate is also characterized in particular by the fact that it is highly elastic and shows a "self-healing" effect (i.e., tears flow shut again).

EXAMPLE 16

The procedure was analogous to that of Example 15, but the almost solvent-free polycondensate of Example 8 was added. The obtained measurement results are compiled in the following Table 3.

TABLE 3

| UV Initiator | Quantity of Initiator (wt. %) | Irradiation Period (s) | Layer Thickness (μM) | Abrasion After 100 Cycles (%) |
|---|---|---|---|---|
| IRGACURE ® 907 | 5 | 0.5 | 20 | 10 |
| IRGACURE ® 367 | 1 | 60 | 20 | 4.5 | modulus of elasticity of the coatings: approximately 2,150 Mpa

For comparison purposes it should be noted that the abrasion after 100 cycles was determined with the Taber abraser for polycarbonate and PVC at 28 or 37%.

EXAMPLE 17

Other compounds were processed into polycondensates of the invention according to the process described in the above examples. The refractive indices ($\eta_D$) and Abbe numbers ($\nu_D$) of some of the polycondensates obtained are compiled in Table 4.

TABLE 4

| Polycondensate from Compound No. (See Preparation Examples) | $\eta_D$ | $\nu_D$ |
|---|---|---|
| 2 | 1.49 | 42-47 |
| 23 | 1.549 | 35-36 |
| 24 (1.25:1 adduct) | 1.587 | 32 |
| 11 | 1.547 | 38.5 |
| 29 | 1.533 | 38 |

EXAMPLE 18

A polycondensate prepared according to the process described in the above examples in almost solvent-free form was converted with 0.5 percent by weight IRGACURE ® 184 (UV initiator), put into a curing mold (diameter 4 cm) and irradiated slowly from the front and the back for approximately 1 minute with an output of 500 or 1,000 W (medium pressure mercury lamp Loctite Uvaloc ® 1000). A cured, transparent molded part (d=5 mm) was obtained. Similar results are obtained with approximately one hour of thermal curing at 60° to 70° C. after the addition of 0.5 to 1.0 percent by weight of t-butyl perneodecanoate.

The following Table 5 shows the refractive indices ($\eta_D$) and the Abbe numbers ($\nu_D$) of some of the molded parts prepared (UV cure).

TABLE 5

| Polycondensate from Compound No. (See Preparation Examples) | $\eta_D$ | $\nu_D$ |
|---|---|---|
| 2 | 1.52 | 47-52 |
| 23 | 1.556 | 35 |
| 24 (1.25:1 adduct) | 1.599 | 33 |

EXAMPLE 19

UV-cured, square-shaped rods were prepared from some of the polycondensates described in the above examples following the addition of 1 percent by weight of IRGACURE ® 184 as the UV initiator. The modulus of elasticity was determined on these rods by the 3-point bending test (universal testing machine UTS-100). The values obtained are compiled in the following Table 6. Occasionally a range of values is given. The exact value depends then on the precise curing conditions.

TABLE 6

| Rods Made of Polycondensate from Compound No. | Modulus of Elasticity (Mpa) |
|---|---|
| 25 | 1,400–19,700 |
| 13 | 65–75 |
| 2 | 1,200–1,300 |
| 22 | 1,100–19,200 |
| 30 | 480 |
| 12 | 2,030 |

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A polycondensate containing unsaturated organic groups, based on hydrolytically condensable monomer compounds of silicon, comprising:

(a) 5 to 100 mole %, based on the monomer compounds, of hydrolytically condensable monomer compounds selected from silanes of the formula (I):

$$\{X_aR_bSi(R'(A)_c)_{(4-a-b)}\}_xB \qquad (I)$$

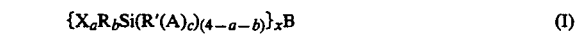

wherein the groups and indices have the following meanings:

X: hydrogen, halogen, hydroxy, alkoxy, acyloxy, alkylcarbonyl, alkoxycarbonyl or —NR''₂;
R: alkyl, alkenyl, aryl, alkaryl, or aralkyl;
R': alkylene, arylene or alkylene-arylene;
R'': hydrogen, alkyl or aryl;
A: S, PR'', POR'', NHC(O)O or NHC(O)NR'';
B: straight chain or branched organic group having at least one unsaturated group and 5 to 50 carbon atoms, wherein said silane of formula I is obtained
(1) by condensing a silane of the formula $X_aR_bSiR'NCO$

wherein (a+b)=3 with a hydroxyl or amino-substituted compound B' having at least one C=C double bond when c=1 and A=NHC(O)O or NHC(O)NR'', or (2) by subjecting a silane of the formula $X_aR_bSiR'Y$

wherein (a+b)=3 and Y is SH, PR''H or POR''H, to an addition reaction with a compound B' having at least two C=C double bonds when C=1 and A=S, PR'' or POR'', or (3) by subjecting a silane of the formula $X_aR_bSiH$

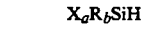

wherein (a+b)=3 to hydrosilylation with a compound B' which is a poly(meth)acrylate containing two or more acrylate groups, methacrylate groups or a combination thereof, when c=0 a: 1, 2 or 3;
b: 0, 1 or 2; wherein the sum (a+b) is equal to three;
c: 0 or 1;
x: whole number, whose maximum value is equal to the number of double bonds in compound B' minus 1, or is equal to the number of double bonds in compound B', when c=1 and A is NHC(O)O or NHC(O)NR''; and (b) 95–0 mole % of monomer compounds hydrolytically co-condensable with and different from said silane of formula (I).

2. The polycondensate of claim 1, wherein the groups and indices have the following meanings:

X: $(C_1-C_4)$-alkoxy or halogen;
R: $(C_1-C_4)$-alkyl;
R': $(C_1-C_4)$-alkylene;
A: S;
a: 1, 2 or 3;
c: 0 or 1;
x: 1 or 2.

3. The polycondensate of claim 1, wherein X is methoxy, ethoxy or chlorine.

4. The polycondensate of claim 1, wherein R is methyl or ethyl.

5. The polycondensate of claim 1, wherein R' is methylene or propylene.

6. The polycondensate of claim 1, wherein A is S.

7. The polycondensate of claim 1, wherein c=1.

8. The polycondensate of claim 1, wherein in formula (I) the unit with the index x is selected from the group consisting of triethoxysilyl, methyl-diethoxysilyl, methyl-dichlorosilyl, 3-methyl-dimethoxysilyl-propylthio, 3-trimethoxysilyl-propylthio, ethoxy-dimethylsilyl-methylthio, and methyl-diethoxysilyl-methylthio.

9. The polycondensate of claim 1, wherein compound B' contains one C=C double bond, c=1 and A=NHC(O)O or NHC(O)NR''.

10. The polycondensate of claim 1, wherein compound B' comprises a (meth)acrylate with two or more acrylate groups, methacrylate groups or a combination thereof.

11. The polycondensate of claim 10, wherein compound B' is selected from the group consisting of acrylates of trimethylolpropane, pentaerythritol, dipentaerythritol, $C_2-C_6$-alkanediols, polyethylene glycols, polypropylene glycols, bisphenol A, substituted bisphenol A or alkoxylated bisphenol A.

12. The polycondensate of claim 1, wherein at least 50 mole percent of the monomer compounds are silicon-containing compounds based on the total of (a) and (b).

13. The polycondensate of claim 12, wherein at least 80 mole percent of the monomer compounds are silicon-containing compounds based on the total of (a) and (b).

14. The polycondensate of claim 1, wherein 25 to 100 mole percent of said monomer compounds (a) and (b) are said silane monomer compounds of formula (I).

15. The polycondensate of claim 14, wherein 50–100 mole percent of said monomer compounds (a) and (b) are said silane monomer compounds of formula (I).

16. The polycondensate of claim 1, wherein said polycondensate contains silicon-containing compounds, which are different from the silanes of formula (I), and which are silanes of the formula (V):

$$X_{a'}SiR_{b'}$$ (V)

wherein X and R are defined as in claim 1, a' is a whole number from 1 to 4 and b' is 0, 1, 2 or 3 and a'+b'=4.

17. The polycondensate of claim 16, wherein a' is a whole number from 2 to 4.

18. The polycondensate of claim 16, wherein b' is 0, 1 or 2.

19. The polycondensate of claim 1, wherein compound B' is a poly(meth)acrylate containing three or more acrylate groups, methacrylate groups or a combination thereof.

20. A process for preparing the polycondensate of claim 1, comprising:
condensing one or more hydrolytically condensable monomer silicon-containing compounds, wherein 5 to 100 mole percent, based on the monomer compounds of the hydrolytically condensable monomers, are selected from the group consisting of silanes of the formula (I):

$$\{X_aR_bSi(R'(A)_c)_{(4-a-b)}\}_xB$$ (I)

wherein the groups and indices have the following meanings:

X: hydrogen, halogen, hydroxy, alkoxy, acyloxy, alkylcarbonyl, alkoxycarbonyl or $-NR''_2$;
R: alkyl, alkenyl, aryl, alkaryl, or aralkyl;
R': alkylene, arylene or alkylene-arylene;
R'': hydrogen, alkyl or aryl;
A: S, PR'', POR'', NHC(O)O or NHC(O)NR'';
B: straight chain or branched organic group having at least one unsaturated group and 5 to 50 carbon atoms, wherein said silane of formula I is obtained (1) by condensing a silane of the formula $$X_aR_bSiR'NCO$$

wherein (a+b)=3 with a hydroxyl or amino-substituted compound B' having at least one C=C double bond when c=1 and A=NHC(O)O or NHC(O)NR'', or (2) by subjecting a silane of the formula $$X_aR_bSiR'Y$$

wherein (a+b)=3 and Y is SH, PR''H or POR''H, to an addition reaction with a compound B' having at least two C=C double bonds when C=1 and A=S, PR'' or POR'', or (3) by subjecting a silane of the formula $$X_aR_bSiH$$

wherein (a+b)=3 to hydrosilylation with a compound B' which is a poly(meth)acrylate containing two or more acrylate groups, methacrylate groups or a combination thereof, when c=0 a: 1, 2 or 3;
b: 0, 1 or 2; wherein the sum (a+b) is equal to three;
c: 0 or 1;
x: whole number, whose maximum value is equal to the number of double bonds in compound B' minus 1, or is equal to the number of double bonds in compound B', when c=1 and A is NHC(O)O or NHC(O)NR''; and (b) 95–0 mole % of monomer compounds hydrolytically co-condensable with and different from said silane of formula (I).

21. The process of claim 20, wherein said condensing step is conducted in the presence of a catalyst or solvent.

* * * * *